US00PP08445P

United States Patent [19]

van Andel

[11] Patent Number: Plant 8,445

[45] Date of Patent: Nov. 2, 1993

[54] ALSTROEMERIA NAMED STAYELOR

[75] Inventor: Jacob van Andel, Aalsmeer, Netherlands

[73] Assignee: Van Staaveren B.V., Aalsmeer, Netherlands

[21] Appl. No.: 889,520

[22] Filed: May 27, 1992

[51] Int. Cl.[5] ..... A01H 5/00

[52] U.S. Cl. ..... Plt./87.1

[58] Field of Search ..... Plt./87.1

*Primary Examiner*—James R. Feyrer

[57] ABSTRACT

A new and distinctive Alstroemeria cultivar particularly distinguished by its medium sized flowers having generally white outer petals tipped with red and medially brushed therefrom with a light pink coloring thus providing a pinkish white appearing background for its inside petals which, in general, have a bright yellow color extending from the base for about three-fourths of the petal length and terminating in a tip end having a pinkish coloration substantially covering an otherwise white body, thus providing a flower having a generally white background for its distinguishing pink and yellow coloration; these flowers being carried on short, strong stems branching in a raceme manner from the upper portion of a tall main stem of a strong upright bush.

1 Drawing Sheet

BACKGROUND OF THE NEW PLANT

This Alstroemeria cultivar originated as a hybrid seedling produced in my nursery at Aalsmeer, Holland by my crossing of two plants, hereinafter identified, selected from a field of various Alstroemeria varieties maintained at my nursery for breeding purposes. This particular seedling was selected from those produced by the said cross-hybrid because of the very unusual flower coloration on a plant having abundant foliage and very favorable growth characteristics. This selected seedling was propagated by me at Aalsmeer by dividing its roots with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing in a raceme manner at the upper end portion of the flowering stem of the plant. The colors shown are as nearly true to those herein specified as is reasonably possible to obtain by conventional photographic procedures.

DESCRIPTION OF THE NEW PLANT

The following is a detail description of my new Alstroemeria plant as observed from plants grown under greenhouse conditions in Aalsmeer, Holland, with the stated flower colors being according to the R.H.S. Colour Chart of The Royal Horticultural Society of London, England.

THE PLANT

Origin: Seedling.

Parentage

*Seed parent.*—Plant number 1327-3.

*Pollen parent.*—Plant number 0333-1.

These parent plants are so identified in my business records of the present cultivar maintained at the office of our Aalsmeer nursery and the production of the aforementioned hybrid and the selected seedling are also there recorded.

Classification:

*Botanic.*—Alstroemeria hybrid.

*Commercial.*—Alstroemeria.

Form: A very tall, upright bush having a strong and vigorous growth habit.

Height: About 250 cm. The plant having a rapid growth rate.

Main stem length: About 180 cm. depending upon the season.

Foliage:

*Quantity.*—Abundant.

*Number of leaves.*—25-35, depending upon the season when observed. Length — 16-21 cm.

*Size and shape of leaf.*—The leaf is of a generally elliptic shape and the average size will also depend upon the season.

*Texture.*—Leathery.

*Color.*—Upper side — Dark Green. Under side — Dark Grey/Green.

Rhizomes:

*Size.*—Varying according to the age of the plant.

*Color.*—White.

THE BUD

Size: Normal.

Shape: Initially pear shaped, becoming generally oblate with expansion and color expansion.

Diameter: About 1-1.5 cm.

Length: About 3-4 cm.

Rate of opening: Normal.

Color of petals: When petal begin to unfurl, RHS 348 with an edge of RHS CC 10-C. The color of the petals when the bud is maturing and opens is the same as the color of the flower when the flower is open.

Peduncle length: 7-8 cm.

Character: Upright.

Color: RHS CC 143 CC.

THE FLOWER

Blooming habit: Continous and profusely all year with peak in May and August. It is not necessary to allow the plant (or rhizomes) to go through the dormant stage to induce blooming.

Size of bloom: Medium.

*Diameter.*—About 6.5 cm.

*Depth.*—About 4.5 cm.

Borne: Singly on a rigid stems containing one to three buds branching outwardly and upwardly from the main stem of the plant.

Shape: When bloom matures, funnel-like.

Petalage:

*Number of petals.*—6.

*Arrangement.*—Two concentric circles each having three petals, the outer petals being triangularly spaced and the inner petals being divided with a pair of them in substantially parallel relation and extending upwardly from the remaining third petal which extends downwardly.

*Form.*—Outer petals — Cuneate with lightly serrated margins. Inner petals — Oblong mucronate apex and entire margins.

*Texture.*—Leathery.

*Appearance.*—Satiny.

*Color.*—Outer petals — RHS 18-B longitudinally brushed with 33-D. The outer petals take an off-white or creamy appearance at maturity. Reverse side — brushed with 34-C/D. Inside petals — both upper and reverse sides body, 12-A with tip of 34-D, the upper side being heavily marked with dark, longitudinal pencil stripes these pencil line markings are localized and appear only on the inner petals.

Discoloration after full bloom: In general, the flower turns to 31-C/D.

Persistence: The flower petals hang on and dry.

Lasting Quality:

*On the plant.*—About 18 days.

*As cut flower.*—About 12 days.

THE REPRODUCTIVE ORGANS

Stamens:

*Number.*—Six.

*Arrangement.*—One opposite each petal.

*Anthers.*—Size: About 8 mm. Color: Orange/-Brown.

*Filaments.*—Length: About 4 cm. Color: Base — White. Tip — Orange/Red.

*Pollen.*—Color: Yellow.

Pistils:

*Number.*—One.

*Style.*—Length: About 4 cm.

*Color.*—Orange/Red.

Character of ovaries:

*Color.*—Orange/Red.

FRUIT

Fertility: The fruit is not fertile.

Shape: Capsular (with no seeds).

Color at maturity: Light Brown.

I claim:

1. A new and distinctive hybrid Alstroemeria plant, substantially as herein shown and described, characterized in particular by its medium sized flowers the outer petals of which are in general of an off-white color with a dark pink mucronate tip and the body longitudinally brushed with pink and the inner petals being of oblong shape and having a yellow color over about three-quarters of the body length marked with many longitudinally extending pencil stripes.

* * * * *

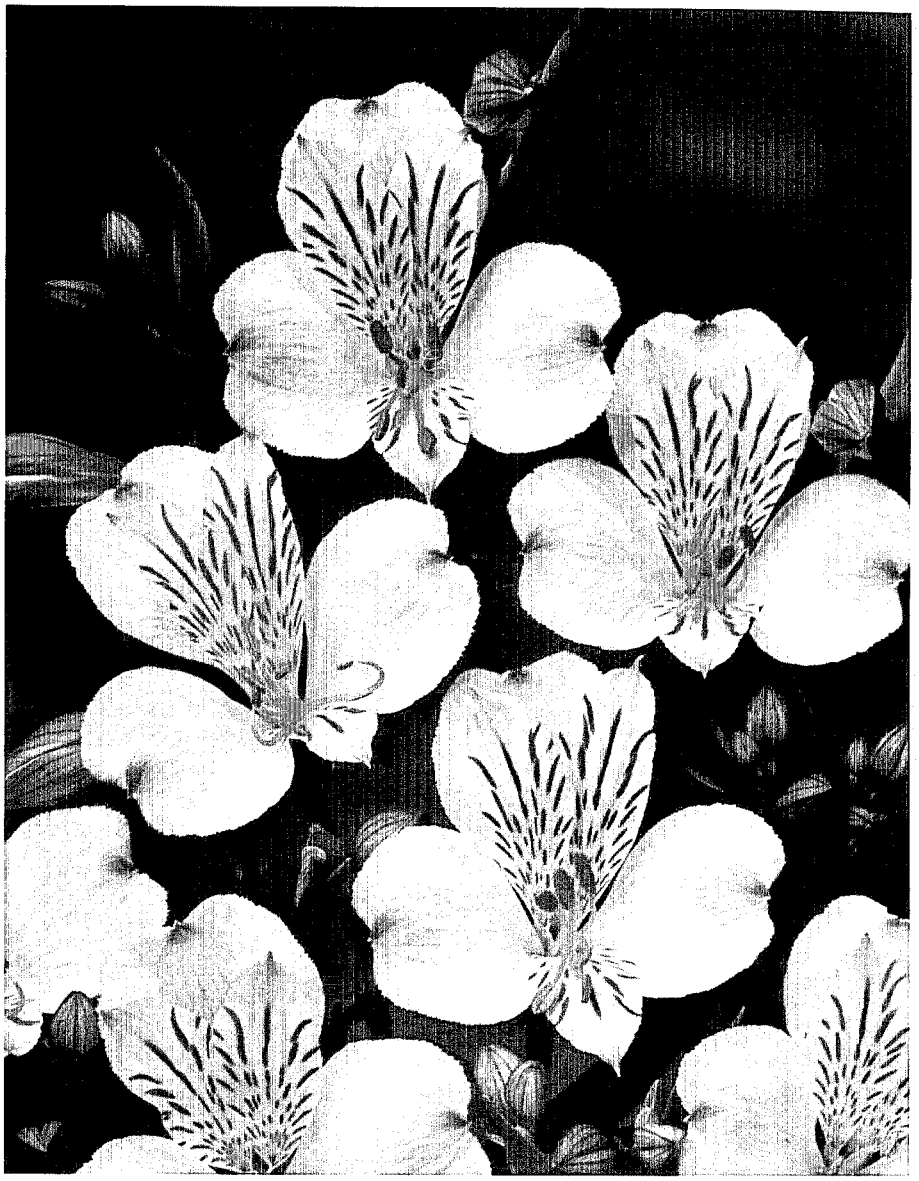

UNITED STATES PATENT AND TRADEMARK OFFICE

CERTIFICATE OF CORRECTION

PATENT NO. : Plant 8,445

DATED : Nov. 2, 1993

INVENTOR(S) : Jacob van Andel

It is certified that error appears in the above-indentified patent and that said Letters Patent is hereby corrected as shown below:

Column 2, line 34, "petal" should read --petals--.
Column 2, line 34, delete "348" and insert --34B--.
Column 2, line 34, "petal" should read --petals--.

Signed and Sealed this

Second Day of August, 1994

*Attest:*

Bruce Lehman

BRUCE LEHMAN

*Attesting Officer*

*Commissioner of Patents and Trademarks*